(12) United States Patent
Bassik et al.

(10) Patent No.: US 7,135,044 B2
(45) Date of Patent: Nov. 14, 2006

(54) MODULAR PROSTHESIS KITS

(75) Inventors: Renen Bassik, Fair Lawn, NJ (US); John D. Czajkowski, Rahway, NJ (US); Thomas F. Mc Carthy, Neshanic Station, NJ (US)

(73) Assignee: Howmedics Osteonics Corp., Mahwah, NJ (US)

( * ) Notice: Subject to any disclaimer, the term of this patent is extended or adjusted under 35 U.S.C. 154(b) by 213 days.

(21) Appl. No.: 10/796,168

(22) Filed: Mar. 9, 2004

(65) Prior Publication Data

US 2005/0203634 A1    Sep. 15, 2005

(51) Int. Cl.
*A61F 2/32* (2006.01)
(52) U.S. Cl. .................................................. 623/22.42
(58) Field of Classification Search ............. 623/22.42, 623/22.4, 22.41, 22.43–22.45, 19.13–19.14, 623/11.11, 20.14–20.15, 22.11–22.19, 19.11–19.12
See application file for complete search history.

(56) References Cited

U.S. PATENT DOCUMENTS

| | | | |
|---|---|---|---|
| 3,722,002 A | 3/1973 | Charnley | |
| 3,938,198 A | 2/1976 | Kahn et al. | |
| 4,031,570 A | 6/1977 | Frey | |
| 4,530,116 A | 7/1985 | Frey | |
| 4,578,081 A | 3/1986 | Harder et al. | |
| 4,608,055 A | 8/1986 | Morrey et al. | |
| 4,664,668 A | 5/1987 | Beck et al. | |
| 4,676,797 A | 6/1987 | Anapliotis et al. | |
| RE32,488 E | 9/1987 | Gustilo et al. | |
| 4,822,370 A * | 4/1989 | Schelhas ................. | 623/22.46 |
| 4,834,758 A | 5/1989 | Lane et al. | |
| 4,846,839 A | 7/1989 | Noiles | |
| 4,857,964 A | 8/1989 | Walker et al. | |
| 4,919,678 A | 4/1990 | Kranz | |
| 4,938,773 A | 7/1990 | Strand | |
| 4,944,763 A | 7/1990 | Willert et al. | |
| 4,957,510 A * | 9/1990 | Cremascoli ............. | 623/22.46 |
| 4,963,155 A | 10/1990 | Lazzeri et al. | |
| 5,002,578 A * | 3/1991 | Luman ................... | 623/22.42 |
| 5,002,581 A | 3/1991 | Paxson et al. | |
| 5,047,060 A | 9/1991 | Henssge et al. | |
| 5,080,685 A | 1/1992 | Bolesky et al. | |

(Continued)

FOREIGN PATENT DOCUMENTS

DE    2 318 396    10/1974

(Continued)

OTHER PUBLICATIONS

Product Catalog; G. Cremascoli S.R.; GSP Cementless Hip Prosthesis (pages).

(Continued)

*Primary Examiner*—Alvin J. Stewart
(74) *Attorney, Agent, or Firm*—Lerner, David, Littenberg, Krumholz & Mentlik, LLP

(57) ABSTRACT

Modular prosthesis kits and systems are disclosed. The kit includes a plurality of stems having a bore therein and a plurality of necks having a tapered distal end adapted to taper lock in the bore of one of the stems. Each neck includes a stem registration element on the distal end of the neck, and each stem includes a neck registration element in an end portion of the bore. The stem registration elements of certain necks and the neck registration elements of certain stems are configured to prevent certain necks from taper locking with certain stems in at least one position, and the stem registration elements of certain necks and the neck registration elements of certain stems cooperate to permit taper locking of certain necks with certain stems.

47 Claims, 13 Drawing Sheets

U.S. PATENT DOCUMENTS

| | | | |
|---|---|---|---|
| 5,100,407 A | 3/1992 | Conrad et al. | |
| 5,139,522 A | 8/1992 | Adrey et al. | |
| 5,181,928 A | 1/1993 | Bolesky et al. | |
| 5,201,882 A | 4/1993 | Paxson | |
| 5,286,260 A | 2/1994 | Bolesky et al. | |
| 5,314,479 A | 5/1994 | Rockwood, Jr. et al. | |
| 5,358,526 A * | 10/1994 | Tornier | 623/19.14 |
| 5,370,706 A | 12/1994 | Bolesky et al. | |
| 5,397,360 A | 3/1995 | Cohen et al. | |
| 5,405,395 A | 4/1995 | Coates | |
| 5,489,309 A * | 2/1996 | Lackey et al. | 623/19.14 |
| 5,507,830 A | 4/1996 | DeMane et al. | |
| 5,580,352 A * | 12/1996 | Sekel | 623/22.46 |
| 5,597,384 A | 1/1997 | Walker et al. | |
| 5,653,764 A * | 8/1997 | Murphy | 623/23.15 |
| 5,653,765 A | 8/1997 | McTighe et al. | |
| 5,702,480 A | 12/1997 | Kropf et al. | |
| 5,702,485 A | 12/1997 | Burke et al. | |
| 5,702,486 A | 12/1997 | Craig et al. | |
| 5,725,592 A | 3/1998 | White et al. | |
| 5,766,263 A | 6/1998 | Grundei et al. | |
| 5,876,459 A | 3/1999 | Powell | |
| 5,902,340 A | 5/1999 | White et al. | |
| 5,906,644 A | 5/1999 | Powell | |
| 5,910,171 A * | 6/1999 | Kummer et al. | 623/18.11 |
| 6,048,365 A | 4/2000 | Burrows et al. | |
| 6,102,956 A | 8/2000 | Kranz | |
| 6,126,694 A | 10/2000 | Gray, Jr. | |
| 6,179,877 B1 | 1/2001 | Burke | |
| 6,190,416 B1 * | 2/2001 | Choteau et al. | 623/22.12 |
| 6,197,062 B1 * | 3/2001 | Fenlin | 623/19.12 |
| 6,200,349 B1 | 3/2001 | Naybour | |
| 6,200,350 B1 | 3/2001 | Masini | |
| 6,224,634 B1 | 5/2001 | Keller | |
| 6,228,120 B1 | 5/2001 | Leonard et al. | |
| 6,228,123 B1 | 5/2001 | Dezzani | |
| 6,238,436 B1 | 5/2001 | Lob et al. | |
| 6,264,699 B1 | 7/2001 | Noiles et al. | |
| 6,273,915 B1 | 8/2001 | Grimes | |
| 6,283,999 B1 | 9/2001 | Rockwood, Jr. | |
| 6,299,648 B1 | 10/2001 | Doubler et al. | |
| 6,306,174 B1 | 10/2001 | Gie et al. | |
| 6,332,896 B1 | 12/2001 | Hubbard et al. | |
| 6,336,941 B1 | 1/2002 | Subba Rao et al. | |
| 6,355,068 B1 | 3/2002 | Doubler et al. | |
| 6,361,566 B1 | 3/2002 | Al-Hafez | |
| 6,368,353 B1 | 4/2002 | Arcand | |
| 6,383,225 B1 | 5/2002 | Masini | |
| 6,428,578 B1 | 8/2002 | White | |
| 6,436,148 B1 | 8/2002 | DeCarlo, Jr. et al. | |
| 6,440,171 B1 | 8/2002 | Doubler et al. | |
| 6,464,728 B1 * | 10/2002 | Murray | 623/22.42 |
| 6,520,994 B1 | 2/2003 | Nogarin | |
| 6,558,425 B1 | 5/2003 | Rockwood, Jr. | |
| 6,610,099 B1 | 8/2003 | Albrektsson et al. | |
| 6,613,092 B1 | 9/2003 | Kana et al. | |
| 6,626,948 B1 | 9/2003 | Storer et al. | |
| 6,682,568 B1 | 1/2004 | Despres, III et al. | |
| 6,702,854 B1 | 3/2004 | Cheal et al. | |
| 6,706,072 B1 | 3/2004 | Dwyer et al. | |
| 6,716,250 B1 | 4/2004 | Ganjianpour | |
| 6,746,487 B1 | 6/2004 | Scifert et al. | |
| 2001/0008981 A1 | 7/2001 | Masini | |
| 2001/0011193 A1 | 8/2001 | Nogarin | |
| 2001/0037152 A1 | 11/2001 | Rockwood, Jr. | |
| 2001/0049561 A1 * | 12/2001 | Dews et al. | 623/19.14 |
| 2001/0051831 A1 | 12/2001 | Subba Rao et al. | |
| 2002/0004685 A1 | 1/2002 | White | |
| 2002/0040244 A1 | 4/2002 | Despres, III et al. | |
| 2002/0052661 A1 | 5/2002 | Spotomo et al. | |
| 2002/0058999 A1 | 5/2002 | Dwyer et al. | |
| 2002/0059000 A1 | 5/2002 | Dwyer et al. | |
| 2002/0072799 A1 | 6/2002 | Despres, III et al. | |
| 2002/0099445 A1 | 7/2002 | Maroney et al. | |
| 2002/0116068 A1 | 8/2002 | McLean | |
| 2002/0120339 A1 | 8/2002 | Callaway et al. | |
| 2002/0120343 A1 * | 8/2002 | Doubler et al. | 623/22.42 |
| 2002/0128720 A1 * | 9/2002 | Masini | 623/22.42 |
| 2002/0133234 A1 | 9/2002 | Sotereanos | |
| 2002/0151984 A1 | 10/2002 | White | |
| 2002/0177900 A1 | 11/2002 | Serbousek et al. | |
| 2003/0014119 A1 | 1/2003 | Capon et al. | |
| 2003/0028253 A1 * | 2/2003 | Stone et al. | 623/19.14 |
| 2003/0033020 A1 | 2/2003 | Hunter et al. | |
| 2003/0074078 A1 | 4/2003 | Doubler et al. | |
| 2003/0074079 A1 * | 4/2003 | McTighe et al. | 623/22.42 |
| 2003/0074080 A1 | 4/2003 | Murray | |
| 2003/0088316 A1 | 5/2003 | Ganjianpour | |
| 2003/0097183 A1 | 5/2003 | Rauscher et al. | |
| 2003/0109933 A1 | 6/2003 | Weissman et al. | |
| 2003/0130740 A1 | 7/2003 | Stocks et al. | |
| 2004/0002759 A1 | 1/2004 | Ferree | |
| 2004/0102854 A1 | 5/2004 | Zhu | |
| 2004/0107001 A1 * | 6/2004 | Cheal et al. | 623/22.42 |
| 2004/0107594 A1 | 6/2004 | Afriat | |

FOREIGN PATENT DOCUMENTS

| | | |
|---|---|---|
| DE | 26 21 666 | 11/1977 |
| DE | 26 46 842 A1 | 4/1978 |
| DE | 0 000 549 | 7/1978 |
| DE | 27 34 249 A1 | 2/1979 |
| DE | 33 40767 A1 | 5/1985 |
| DE | 44 07 227 A1 | 9/1995 |
| EP | 0 201 407 | 4/1986 |
| EP | 0 257 359 | 8/1986 |
| EP | 0 243 298 | 4/1987 |
| EP | 597553 | 5/1994 |
| FR | 2 295 729 | 12/1974 |
| FR | 2 575 383 | 12/1984 |
| FR | 2 580 926 | 4/1985 |
| FR | 2 640 497 | 12/1988 |
| FR | 2 481 596 | 4/1990 |
| FR | 2686789 | 1/1992 |
| FR | 2 701 836 A | 9/1994 |
| FR | 2 729 292 A | 7/1996 |
| JP | 7 227401 | 8/1995 |
| WO | WO-03094803 | 5/2003 |

OTHER PUBLICATIONS

Toni et al., Anatomic cementless total hip arthroplasty with ceramic bearings and modular necks: 3 to 5 years follow-up, Hip International, vol. 11 No. 1, pp. 1-17, Copyright by Wichtig Editore, 2001.

JISRF/Apex Study Group Members, New Proximal "Dual Press™" Modular Stem Design, JISRF Update, Joint Implant Surgery & Research Foundation, pp. 4-7.

OTI Osteoimplant Technology, Inc., IMIN(TM) Series, R120(TM) Modular Total Hip System Cemented, Product Information, 1 page.

OTI Osteoimplant Technology, Inc., R120 IMIN(TM) Series Modular Hip Systems, website address: http://www.osteoimplant.com/hips_r120.shtml, 2 pages.

McTighe, Ph. D., JISRF Update, Joint Implant Surgery & Research Foundation, Cementless Modular Stems, Product Review, 11 pages, May 2002.

The Total System, Instrumentation—Harris Precoat, Zimmer Product Catalog, 1987, 6 pages.

\* cited by examiner

MODULAR PROSTHESIS KITS

FIELD OF THE INVENTION

The present invention relates to modular prosthesis kits and systems. More particularly, the present invention relates to modular prosthesis systems including stems that allow standard prosthesis stems and heads to be interconnected in a variety of configurations and prevents certain combinations of necks and stems.

BACKGROUND OF THE INVENTION

Conventional shoulder and hip prostheses typically were unitary structures including an integral stem and neck interconnecting a head. These types of prostheses involve the insertion of the stem in a cavity formed in the femur for a hip prosthesis, or in the humerus for shoulder prosthesis. A problem associated with conventional shoulder and hip prostheses is the need to maintain large inventories of differently configured prostheses for different patient anatomies. Prostheses having a variety of different head sizes, different stem sizes, and different neck angles and radial offsets between the head and stem are required to be kept on hand. Various configurations are required for each size category.

To reduce the required inventory of parts, assorted modular prostheses have been provided. Such systems include differently sized necks, heads and necks with different lengths and angles. While existing modular prosthesis systems allow flexibility with respect to either the neck angle or the radial offset between the head and the stem to accommodate each patient's unique anatomical requirements, improvements are still needed. Some combinations of stems and necks result in a prosthesis that may fail. If the prosthesis fails, the patient must undergo a second operation to remove the failed prosthesis and insert a new prosthesis. It would be desirable to provide a kit and a system comprising a plurality of different sized stems and necks of different lengths and angles that prevent combinations of certain necks with certain stems to prevent failure of the prosthesis.

SUMMARY OF THE INVENTION

In accordance with one or more embodiments of the present invention, modular prosthesis kits and systems are provided. It will be understood that while the drawings show prostheses for a hip, the prosthesis kits and systems of the present invention may also include shoulder prosthesis. As used herein, the term distal refers to a portion of the prosthesis further from the patient's heart, and proximal refers to a portion of the prosthesis closer to the patient's heart.

According to one or more embodiments, a kit or a system comprises at least two differently sized or configured stems, each stem including a tapered bore having a distal portion and a proximal portion and a neck registration element located in the distal portion of the bore and a plurality of necks. Each of the necks has a proximal end and a distal end, the distal end including a conically tapered portion configured to taper lock in the tapered bore. Each neck also includes a stem registration element extending from the distal end. The plurality of necks includes first neck including a stem registration element that cooperates with the neck registration element of at least one stem to permit the first neck to taper lock in the bore of at least one stem in one position and to prevent the first neck from taper locking in the bore of at least one stem in at least one position.

In certain embodiments, the plurality of necks further includes at least one non-fitting neck having a stem registration element that prevents the at least one non-fitting neck from taper locking in the bore of at least one of the stems in any position. In other embodiments, the plurality of necks includes at least one fitting neck having a stem registration element that permits the at least one fitting neck to taper lock in the bore of the at least one of the stems in at least two positions. According to certain embodiments the plurality of necks includes at least one non-fitting neck having a stem registration element that prevents the at least one non-fitting neck from taper locking in the bore of at least one preselected stem.

In one or more embodiments, the stem registration element of a first neck includes a shaped tab extending longitudinally from the distal end of the neck and the neck registration element includes a shaped slot in the distal portion of the bore such that the tab of the first neck can register with the slot of at least one of the stems to allow the tapered end portion of the first neck to taper lock in the bore of the stem in at least one position and the tab of the first neck cannot register in the slot of the at least one stem to prevent the tapered end portion of the first neck from taper locking in the bore of at least one stem in one position. In some embodiments, the tab of the first neck is elongated in one direction from the center of the tapered end of the neck such that the tab cannot register with the slot in the bore of at least one stem and prevents taper locking of the tapered end of the at least one first neck in the bore of at least one stem in at least one position. In some embodiments, the slot in the bore of at least one stem and the tab of the first neck are configured to register such that the tapered end of the first neck can taper lock in the bore of at least one stem in at least one position. In certain embodiments, the slot of at least one of the stems is elongated in one direction with respect to the center of the bore.

In one or more embodiments, each of the shaped slots of the at least one stem have a major axis and a minor axis and the each of the tabs of the first necks have a major axis and a minor axis. For example, the tabs and slots can be elliptical in cross-section. However, it will be understood, the tabs and slot can have other cross-section shapes such as rectangular, oblong, diamond, etc. In certain embodiments, the tab and the slot are substantially the same size in cross-section.

In one or more embodiments, the stem registration element of each neck includes a shaped tab extending longitudinally from the distal end of the neck and the neck registration element of each stem includes a shaped slot, wherein the tab of at least one of the non-fitting necks and the slot of the at least one stem are configured such that the tab of at least one of the non-fitting necks cannot register in the slot of at the at least one of the stem to prevent the tapered end of the non-fitting neck to taper lock. In some embodiments, the tab of the non-fitting neck is larger than the slot of the at least one stem in at least one dimension. In at least one embodiment, the tab has a length dimension and the slot has a depth dimension, and the length of the tab of the at least one non-fitting neck is greater than the depth of the slot of at least one stem. According to certain embodiments, the slots have a major axis and a minor axis and the tabs have a major axis and a minor axis. For example, the tabs and the slots may be elliptical in cross section. In some embodiments, the major axis of the tab of the at least one non-fitting neck is larger in size than the major axis of the slot of at least one stem. In certain embodiments, the minor axis of the tab of at least one non-fitting stem is greater in size than the minor axis of the slot of at least one stem. According to certain embodiments, the tab on the at least one non-fitting neck has a different shape than the slot of at least one of the stems.

According to some embodiments, the stem registration element of each neck includes a shaped tab extending longitudinally from the distal end of the neck and the neck registration element of each stem includes a shaped slot, wherein the tab of the at least one of the fitting necks and the slot of the at least one stem are configured such that the tab of at least one of the fitting necks can register in the slot of at least one of the stem in multiple positions to permit the tapered end of the at least one fitting neck to taper lock in the bore of the at least one stem. In certain embodiments, the tab of the at least one fitting neck and the slot of the stem each has a major axis and a minor axis. In some embodiments, the size of the tab of the at least one fitting neck and the slot of at least one of the stems are substantially the same. According to certain embodiments, the tab of the at least one fitting neck is smaller in at least one dimension that the slot of the at least one stem. In some embodiments, the stem registration element of each neck includes a slot and the neck registration element of each stem includes a tab.

Other embodiments of the invention relate to a modular prosthesis system comprising a plurality of differently sized stems, each stem including a tapered bore having a distal portion and a proximal portion and a neck registration element on the distal portion of the bore and a plurality of necks having different lengths and angles, each of the necks having a conical taper on a distal end of the neck configured to taper lock in the tapered bores. A stem registration element longitudinally extends from the distal end of each neck, wherein a first neck of a predetermined length and angle has a stem registration element that can register with the neck registration element of at least one of the stems in only one position to permit the first neck to taper lock with bore of the at least one stem in only one position. A second neck of a predetermined length and angle has a stem registration element that can register with at least one of the necks in multiple positions and permit the second neck to taper lock in the bore of the at least one stem in multiple positions.

Certain embodiments include a third neck of a predetermined length and angle having a stem registration element that cannot register with the neck registration element of at least one stem in any position preventing taper locking of the third neck with the at least one stem in any position. As in the previously described embodiments, the stem registration element can include a shaped tab and the neck registration element can include a shaped slot. The tab of the first neck may be elongated in one direction or offset with respect to the center of the tapered end of the neck to prevent registration with a slot of at least one stem. In other embodiments, the tab of the second neck is smaller than the slot in at least one dimension. The tab and slot can have a cross-sectional shape with a major axis and a minor axis. For example, the tab and slot have an elliptical cross-sectional shape. In certain embodiments, the major axis of the tab is shorter than the major axis of the slot. The cross-sectional shape and size of the tab and the slot can be substantially similar.

According to some embodiments, the tab of the third neck is larger in one dimension than one dimension of the shaped slot of at least one stem. For example, the tab of the third neck has a length dimension that is greater than the depth of the shaped slot of at least one stem. The shaped tab of the third stem and the shaped slot of at least one stem each may have a major axis and a minor axis.

Another embodiment relates to a modular prosthesis kit comprising at least two differently sized stems, each stem including taper bore having a distal portion and a proximal portion and a neck registration element on the distal portion of the bore and a plurality of necks. Each neck has a tapered distal end and a stem registration element on the distal end of the neck, wherein the plurality of necks includes a first neck having a stem registration element that can register with the neck registration element of at least one stem in more than one position, a second neck having a stem registration element that can register with the neck registration element of at least one stem in only one position, and a third neck having a stem registration element that cannot register with at least one neck in any position.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF EXEMPLARY EMBODIMENTS

Figure 1A:
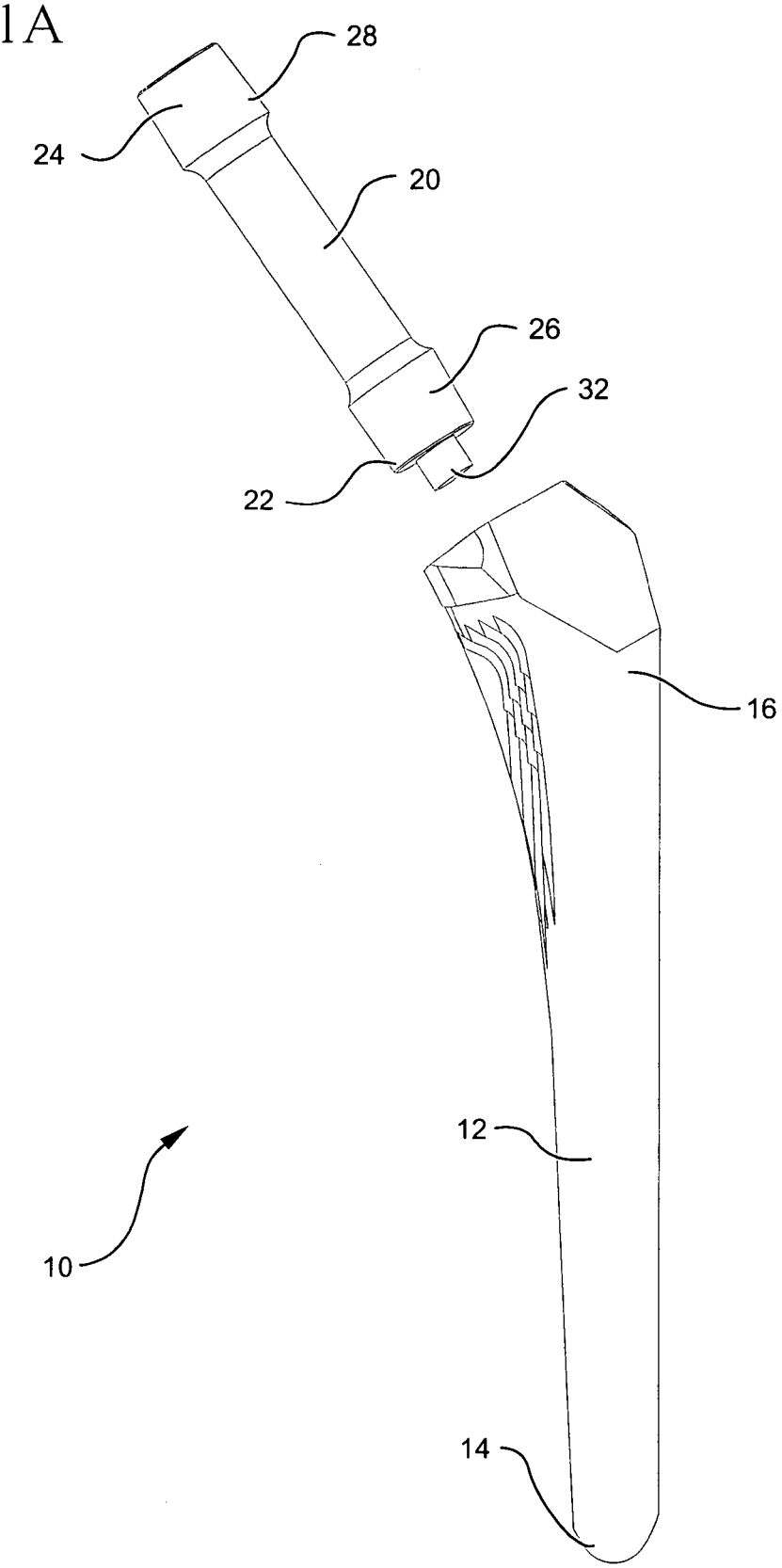
FIG. 1A is a lateral perspective view of a stem and neck according to one embodiment.

Before describing several exemplary embodiments of the invention, it is to be understood that the invention is not limited to the details of construction set forth in the following description. The invention is capable of other embodiments and of being practiced or carried out in various ways.

Referring now to the Figures, and in particular FIG. 1, a modular prosthesis 10 is shown. The modular prosthesis includes a stem 12 including a distal end 14 and a proximal end 16. The proximal end 16 of the stem 12 includes a bore 18 therein. The modular prosthesis also includes a neck 20 having a distal end 22 and a proximal end 24. The distal end 22 includes has a conical taper portion 26, and the proximal end 24 also includes a taper portion 28. The taper portion 28 on the proximal end is configured for a taper lock fit with a head having a bore therein (not shown).

The present invention relates to modular prosthesis kits and systems. According to one or more embodiments, a kit comprises a plurality of stems and a plurality of necks. The necks and stems include complementary registration features that permit a first neck to taper lock with at least one of the stems in multiple positions, and a second neck has a registration feature that prevents taper locking of the second neck in the bore of at least one stem in one position. In certain embodiments, at least a third neck is provided having a registration feature that prevents the third neck from taper locking in the bore of at least one stem in any position. One or more embodiments of the present invention provides kits and systems that prevents a practitioner from assembling improper combinations of stems and necks that would fail when implanted in a patient. These improper combinations are determined by laboratory testing of combinations of necks and stems and/or finite element modeling as is known in the art. Certain embodiments of the present invention provide a relatively simple and foolproof way of preventing improper combinations of components.

Figure 1B:
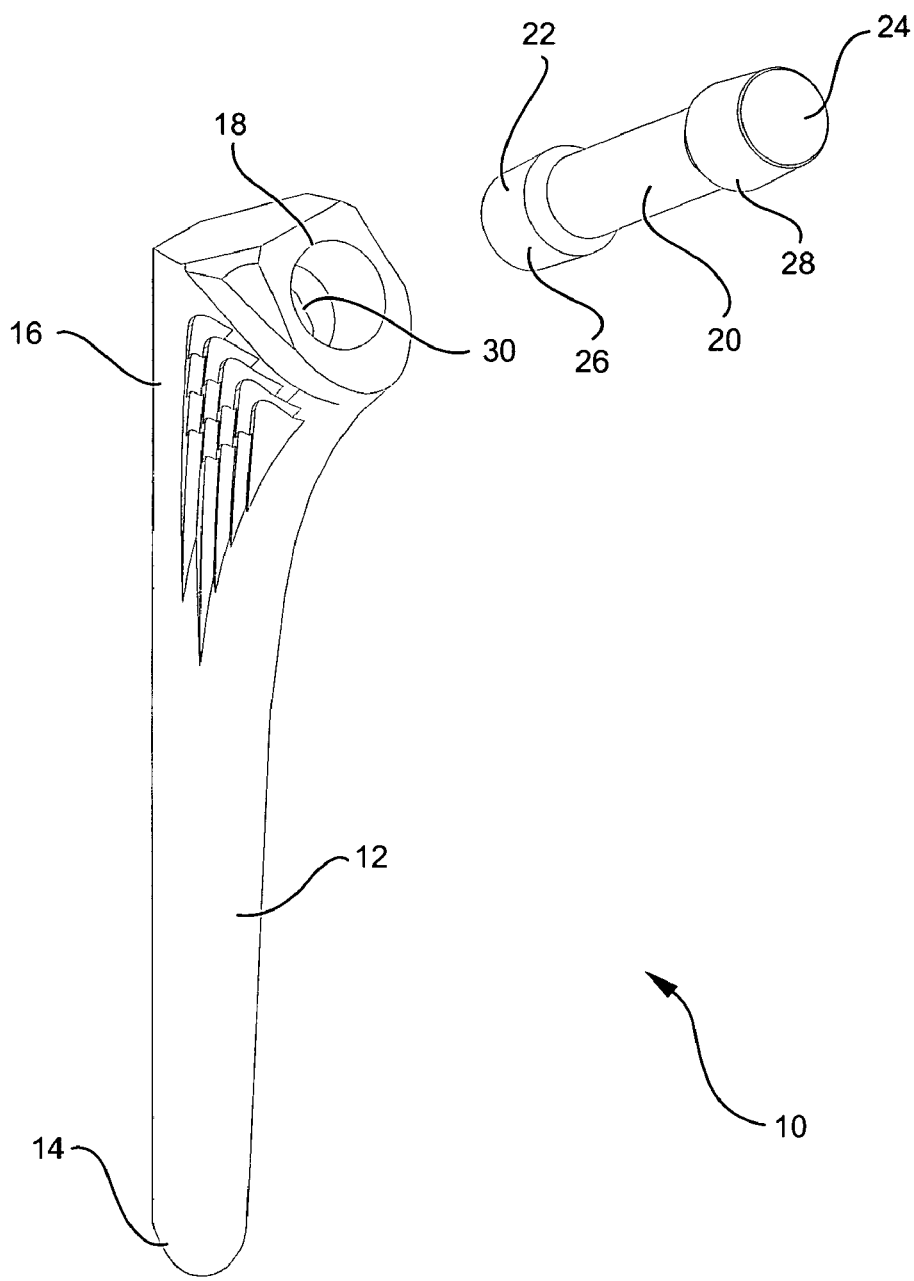
FIG. 1B is a medial perspective view of a stem and neck according to one embodiment.
Figure 2:
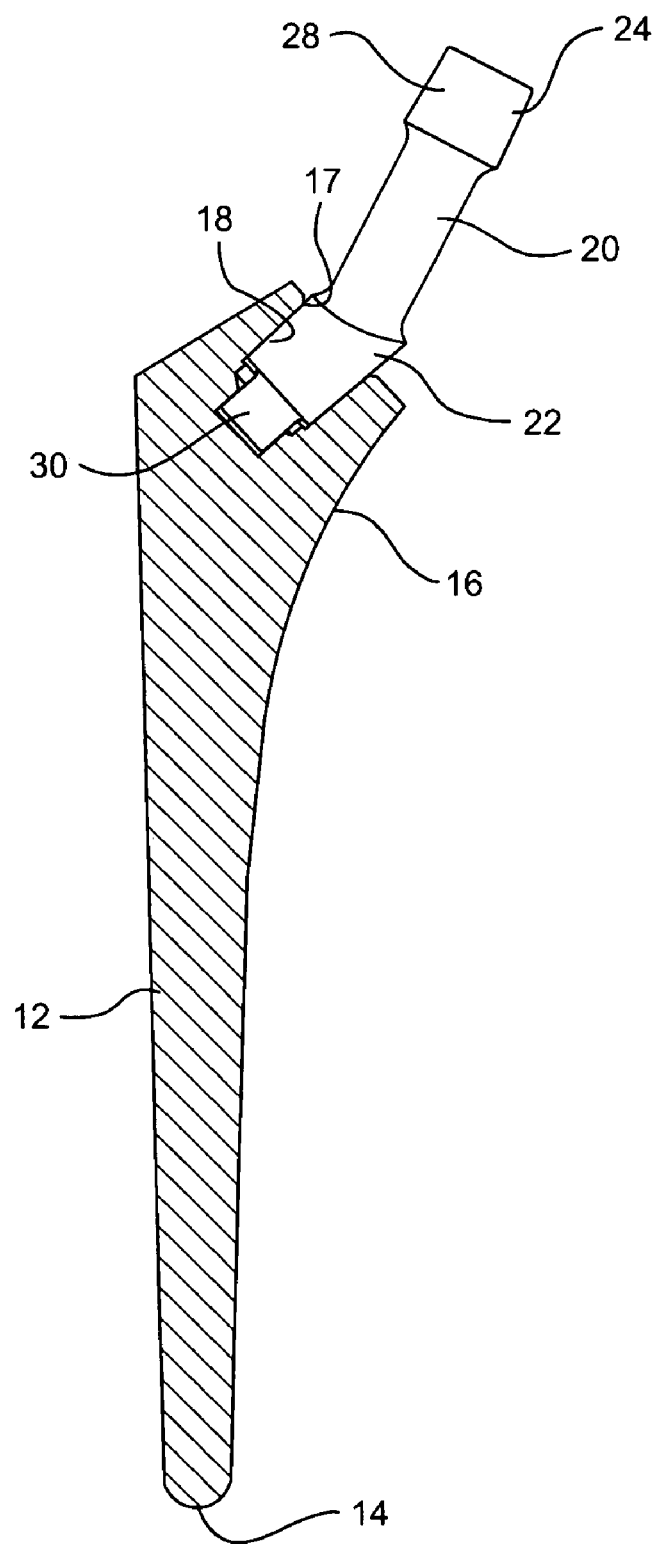
FIG. 2 is a cross-sectional view of a modular prosthesis according to one embodiment.

According to one embodiment, a kit includes at least one stem 12 of the type shown in FIGS. 1A, 1B and 2, which has a distal end 14, a proximal end 16 and a bore 18. The bore 18 has a proximal portion 17 and a distal portion 19. The bore 18 preferably has a conical taper such that the radius of the bore is greater near the proximal portion 17 of the bore than the radius of the bore at the distal portion 19. A neck registration element 30 is located in the distal portion 19 of the bore 18. Preferably, the neck registration element 30 of some of the stems has a common axis with the bore, and in certain embodiments, is coaxial with the bore. The neck registration element 30 in the embodiment shown in FIGS. 2 and 3 includes a slot. In certain preferred embodiments, the kit preferably includes at least two differently sized stems, and certain necks will be able to taper lock with certain stems in at least one position, and certain necks may be prevented from taper locking with certain stems as will be described in more detail below. Each kit also includes a plurality of necks 20. In certain embodiments, the necks 20 are different sizes or lengths and have different angles.

Each of the necks 20 has a distal end 22 and a proximal end 24, the distal end 22 including a tapered portion 26 configured to taper lock in the tapered bore 18 and a stem registration element 32 extending from the distal end 22. The tapered portion 26 and the bore 18 may be conically tapered. Preferably, the stem registration element 32 of at least one of the necks has a common axis with the distal end 22 of the neck 20, and in certain embodiments, the stem registration element 32 is coaxial with the distal end 22. The tapered portion 26 of the neck 20 is configured to taper lock in the bores 18 of the stems, however, according to one embodiment of the present invention, certain necks 20 will be prevented from taper locking with certain stems 12 in certain circumferential positions, certain necks will be permitted to taper lock with certain stems in at least two circumferential positions, and certain necks will not be permitted to taper lock with certain stems in any circumferential position. Impermissible combinations of certain stems with certain necks in certain positions will be predetermined beforehand by testing or modeling.

Figure 3:
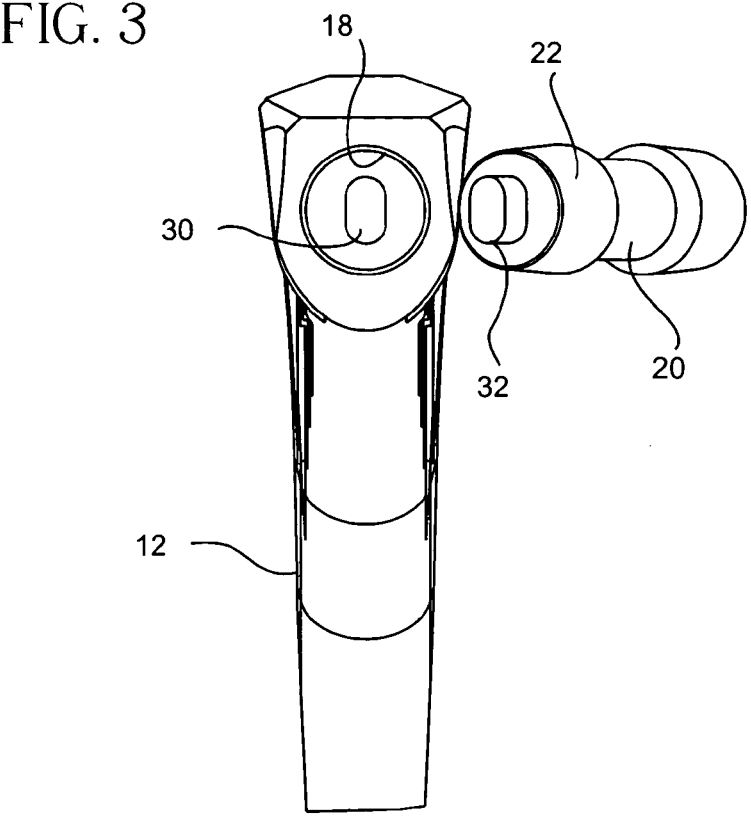
FIG. 3 is an partial perspective view of a stem and a neck according to one embodiment in which a tab protruding from the distal end of the neck can register with a slot in the stem.
Figure 3A:
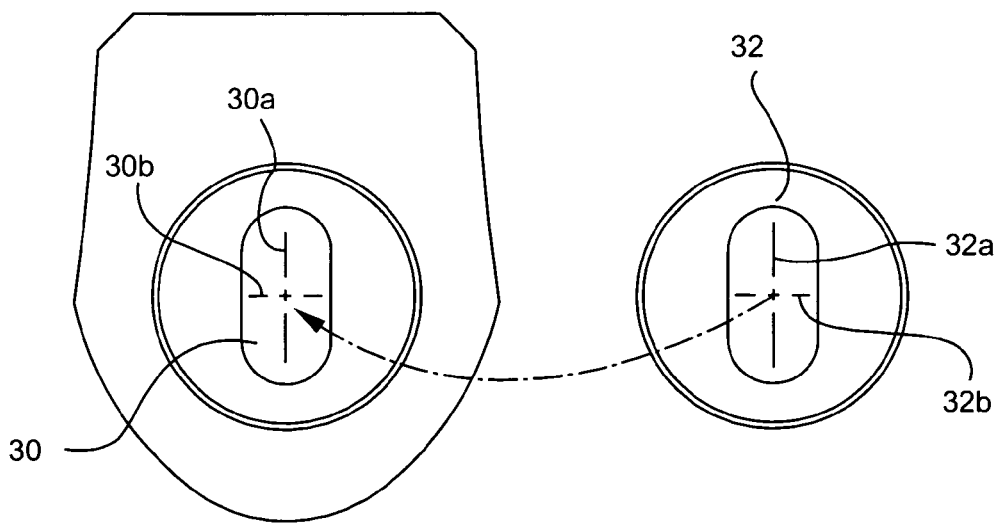
FIG. 3A is a plan view of the tab on the neck and slot in the stem of the stem and neck shown in FIG. 3.

A perspective view of a neck and stem is shown in FIG. 3 and FIG. 3A shows a plan view of a portion of the neck 20 and stem 12. A stem 12 includes a bore 18, and a neck registration element 30 in the form of a slot located in the bore 18. Preferably, the neck registration element 30 has a common axis with the bore 18, and in some embodiments, the neck registration element 30 is coaxial with the bore 18. The neck 20 has a tab 32 extending longitudinally from the distal end 22 of the neck. Preferably, the tab 32 has a common axis with the distal end 22, and in certain embodiments, the tab 32 and the distal end 22 of the neck may be coaxial. In the combination shown, the tab 32 and the slot 30 are approximately the same size, and the tab 32 and slot 30 are each coaxially located with respect to the bore 18. The slot 30 has a major axis 30a and a minor axis 30b. The tab 32 also has a major axis 32a and a minor axis 32b. The size of the slot 30 and the tab are substantially the same so that the tab 32 can register with the slot 30 of at least one stem in more than one position and permit the neck 20 and stem 12 to taper lock. As shown in FIG. 3, the tab 32 can register with the slot 30 to permit the neck 20 and the stem 12 to taper lock in the position shown. The neck 20 can also be rotated 180 degrees about the longitudinal axis of the neck and the tab 32 can register with the slot 30 in a second position as well.

Figure 11:
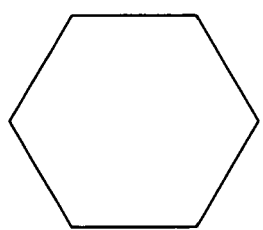
FIG. 11 is a plan view showing examples of alternate cross-sectional shapes of the tabs and slots.
Figure 11:
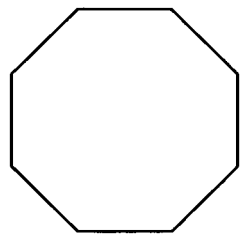
Figure 11:
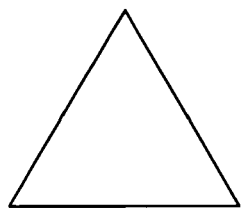
Figure 11:
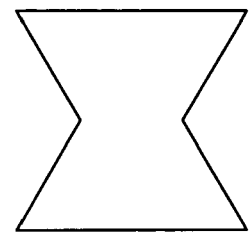
Figure 11:
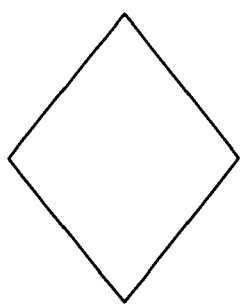
Figure 11:
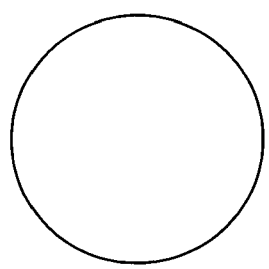
Figure 11:
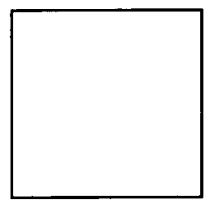
Figure 11:
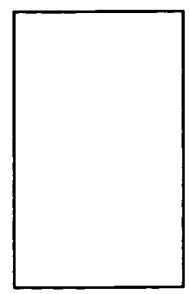

In the embodiment shown in FIG. 3, the tab 32 and the slot 30 are elliptical in cross-section, however, the tab and slot could have other configurations such as a cross-sectional shape that is square, triangular, rectangular, polygonal, hexagonal, octagonal, circular, diamond-shaped, or shaped like a bow-tie. These shapes are shown in FIG. 11, and it will be understood that other cross-sectional shapes are within the scope of the invention.

Figure 4:
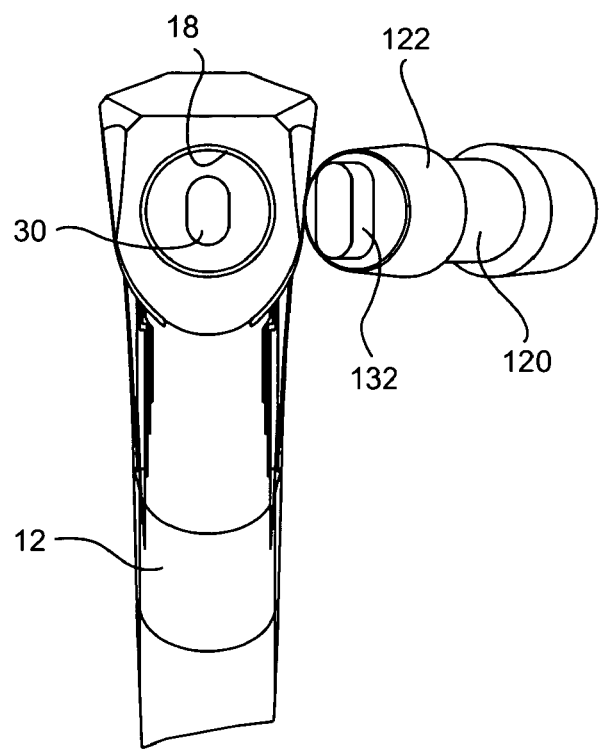
FIG. 4 is a partial perspective view of a stem and a neck according to an alternate embodiment in which a tab on the distal end of the neck is larger than a slot in the neck and prevents registration of the tab in the bore.
Figure 4A:
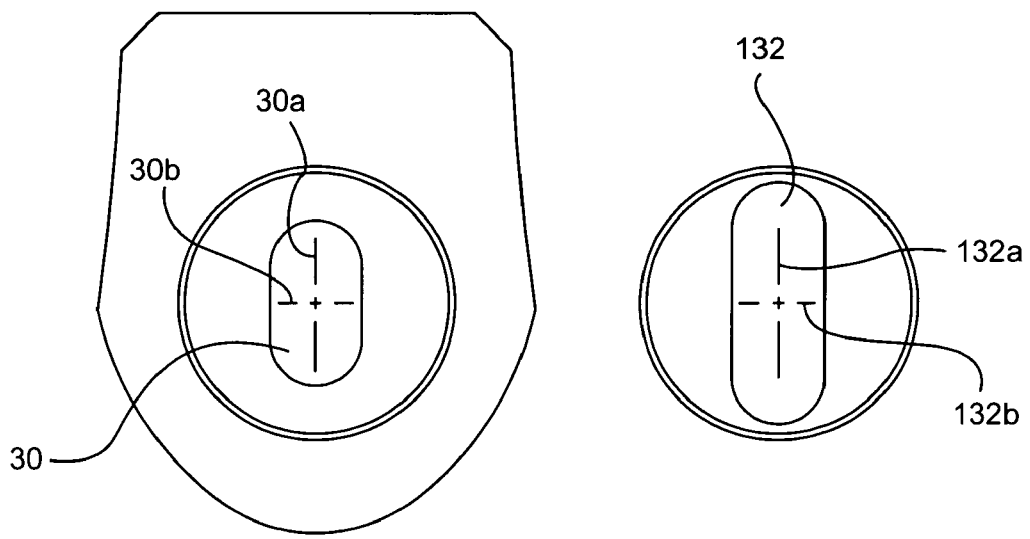
FIG. 4A is a plan view showing the tab on the neck and slot in a bore of the stem of the stem and neck shown in FIG. 4.

Referring now to FIGS. 4 and 4A, a second possible neck and stem combination is shown. In FIGS. 4 and 4A, components that are substantially similar to the components shown in FIGS. 3 and 3A are designated with by the same reference numeral in the 100 series. The stem 12 in FIG. 4 is the same stem 12 shown in FIG. 3 and has a bore 18 with a neck registration element in the form of a slot 30 therein. The slot 30 and the bore 18 are coaxial to each other. A neck 120 includes a distal end 122, and a stem registration element in the form of a tab 132 located on the distal end 122. In the combination shown, the tab 132 is sized slightly larger than the slot 30 in at least one dimension. The slot 30 has a major axis 30a and a minor axis 30b. The tab 132 also has a major axis 132a and a minor axis 132b. In the embodiment shown, the major axis 132a of the tab 132 is larger than the major axis 30a of the slot 30. It will be understood that the minor axis 132b of the tab 132 could be larger than the minor axis 30b of the slot 30, while the major axes 30a and 132a remain approximately equal in size. Because the tab 132 is sized larger than the slot 30 in at least one dimension, in particular along the major axes 132a, the tab 132 cannot register with the slot 30, thus preventing the tapered distal end 122 of the neck 120 from taper locking in the bore 18 of the stem 12 in any position.

The modular stem and neck combination shown in FIG. 3 and the modular stem and neck combination shown in FIG. 4 can be combined to provide a kit comprising the neck 120 that cannot taper lock with stem 12 and the neck 20 that can taper lock with stem 12. Thus, combining the stem and neck combinations in FIGS. 3 and 4 provides a kit, which comprises a neck 20 that fits and taper locks with stem 12 and a neck 120 that does not fit and taper lock with the stem 12.

Figure 5A:
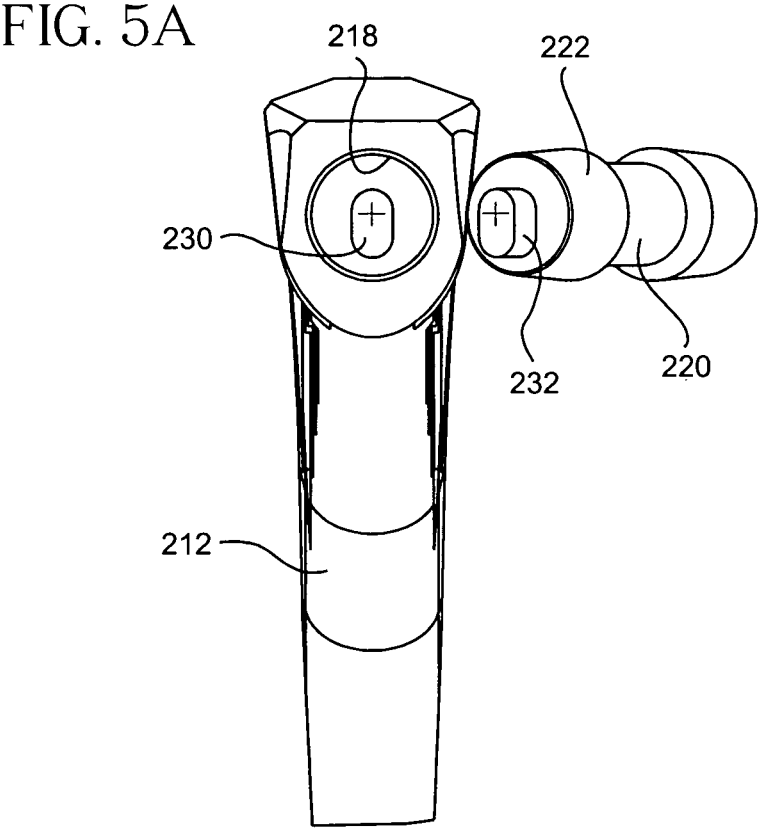
FIG. 5A is a partial perspective view of a stem and a neck according to an alternate embodiment in which a tab on the neck is elongated in one direction from the center of the neck and a slot is elongated in one direction from the center of the bore in the stem.
Figure 5B:
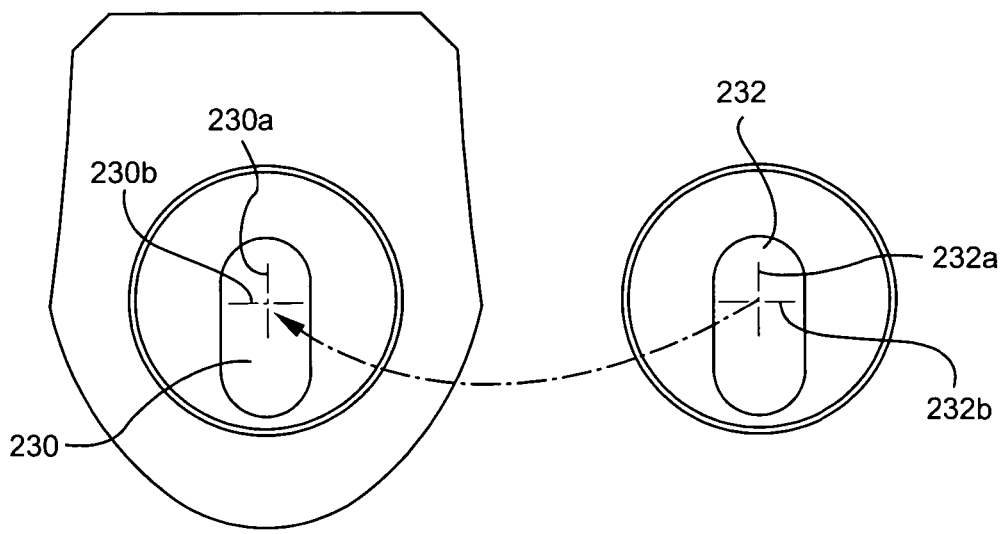
FIG. 5B is a plan view showing the tab on the neck and the slot in the bore of the stem of the stem and neck shown in FIG. 5A.
Figure 5C:
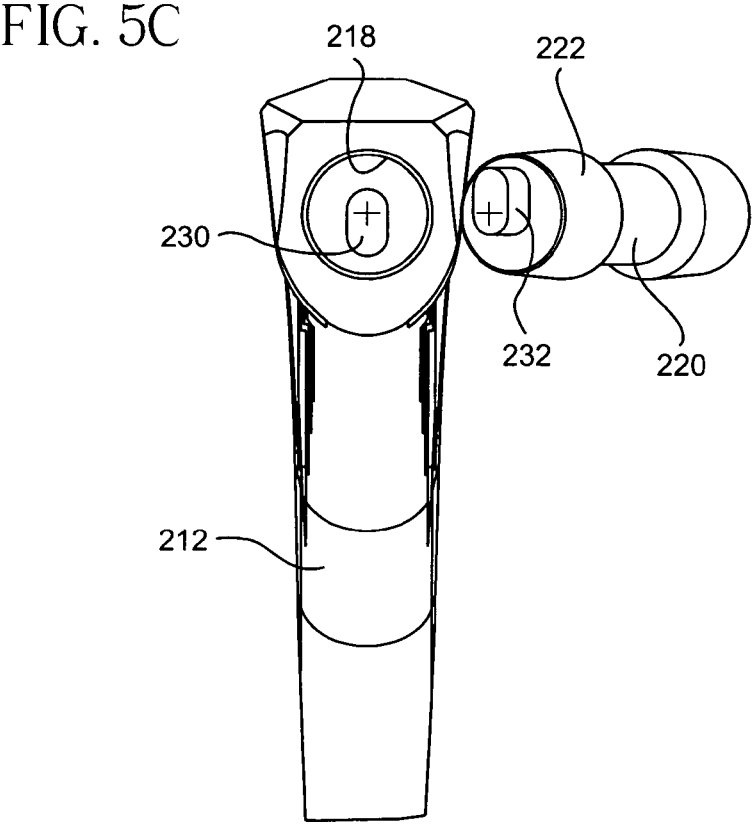
FIG. 5C is a partial perspective view of the stem and neck shown in FIG. 5A with the neck rotated 180 degrees about its longitudinal axis such that the tab and the slot are misaligned and cannot register.
Figure 5D:
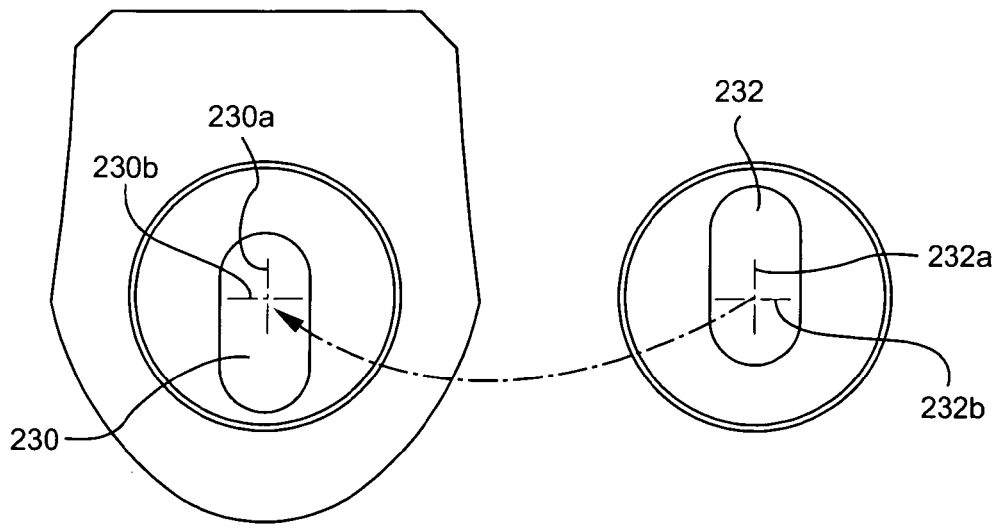
FIG. 5D is a plan view showing the misalignment of the tab on the neck and the slot in the bore of the neck.

FIGS. 5A through 5D show yet another combination of a stem and neck. Components that are similar to the components in FIGS. 3 and 4 are designated with like reference numerals in the 200 series. FIGS. 5A–5D show a neck 220 having a tab 232 extending longitudinally from the distal end 222 of the neck. The tab 232 and the distal end 222 are eccentric to each other. Stated another way, a portion of the tab is longer in one direction with respect to the central axis of the end of the neck 220, such that the tab 232 is offset from the center of the distal end 222 of the neck 220. A stem 212 includes a bore 218, and a neck registration element 230 in the form of a slot located in the bore 218. The slot 230 is eccentric with respect to the center of the bore 218. In other words, a portion of the slot 230 is longer in one direction with respect to the center of the bore 218 such that the slot 230 is offset from the center of the bore 218. The slot 230 has a major axis 230a and a minor axis 230b. The tab 232 has a major axis 232a and a minor axis 232b. In the combination shown, the tab 232 and the slot 230 are approximately the same size. In the arrangement shown in FIGS. 5A and 5B, the tab 232 is elongated along its major axis in one direction with respect to the tapered end portion 222 and the slot 230 is elongated along its major axis in the same direction with respect to the center of the bore 218 such that the tab 232 can register with the slot 230 in only the position shown, permitting the neck 220 to taper lock in the bore 218 of the stem 212. In FIGS. 5C and 5D, the neck 220 is shown rotated 180 degrees about its longitudinal axis. In the arrangement shown in FIGS. 5C and 5D, the tab 232 and the slot 230 cannot register, preventing the neck 220 from taper locking in the bore 218 of the stem 212. In the embodiment shown in FIGS. 5A–5D, the neck 220 thus fits in the bore 218 of the stem in only one position. Such a configuration in which a neck can fit in a stem in only one angular or circumferential position may be desirable when long, high angle necks are combined with certain sized stems to prevent a combination that would fail when implanted in a patient. As discussed above, such combinations are determined beforehand by actual testing or using modeling such as finite element modeling.

The neck and stem combinations shown individually in FIGS. 3–3A, 4–4A and 5A–5D can be combined together to provide a kit or a system of stems and necks including three alternate necks 20, 120 and 220 and two alternate stems 12 and 212. It will be appreciated that other stem and neck elements could be included in the kit to increase the range of combinations.

Figure 6A:
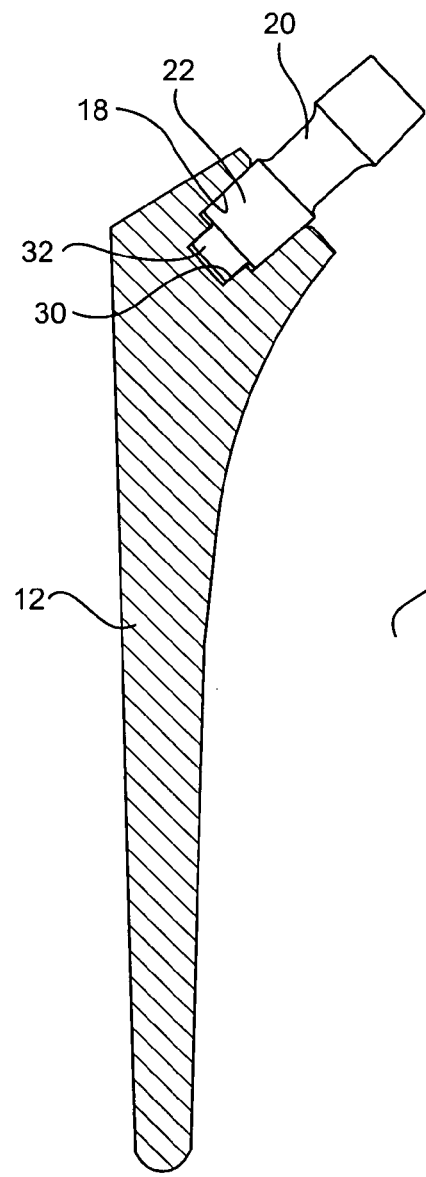
FIG. 6A is a cross-sectional view of a neck fitted into a stem in which a tab on the neck and a slot in the stem are sized so that the tab registers with the slot.
Figure 6B:
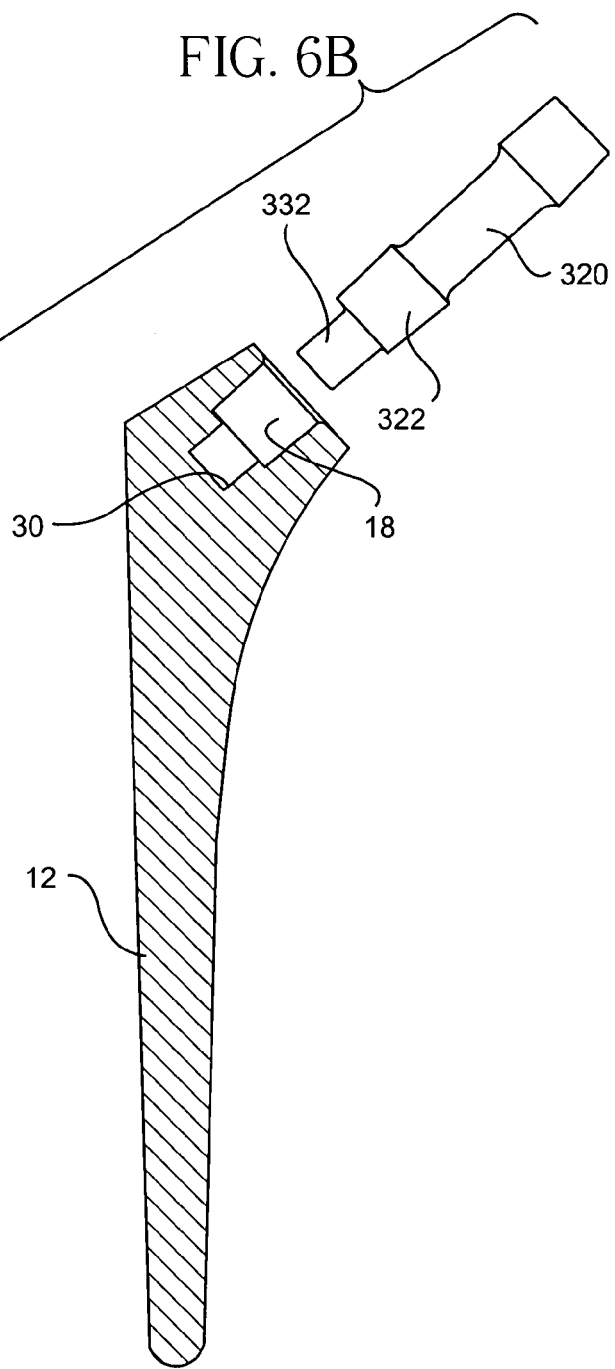
FIG. 6B is a cross sectional view a neck having an elongated tab that cannot register in a slot in a stem that is shorter than the tab.

Referring now to FIGS. 6A and 6B, a further variation of the neck registration element and stem registration elements is presented. In FIG. 6A, the tab 32 and slot 30 of their respective neck 20 and stem 12 can register and permit the neck 20 and stem 12 to taper lock. In FIG. 6B, the tab 332 and slot 30 of their respective neck 320 and stem 12 cannot register, preventing the neck 320 and stem 12 from taper locking. In FIG. 6A, the stem 12 is similar to the stem shown in FIG. 2. The stem 12 includes a bore 18 and a neck registration element in the form of a slot 30 coaxially located in the bore 18. The neck 20 is similar to the neck shown in FIG. 2. The neck 20 includes a tab 32 extending longitudinally from a distal, tapered end 22 of the neck 20. As in the embodiment in FIG. 2, the tab 32 is coaxial with the distal end 22 of the neck 20.

In FIG. 6B, the stem 12 is the same as the stem in FIG. 6A. The neck 320, however, includes a tab 332 extending longitudinally from a distal end 322 of the neck 320 that has been lengthened with respect to the longitudinal axis of the neck 220. The tab 332 is coaxial with respect to the distal end 322 of the neck 320. The depth of the slot 30 is less than the length of the tab 332 along the longitudinal axis, preventing the stem 12 from taper locking with the neck 320. The stem and neck combination shown in FIG. 6B can be included with the stem and neck combinations shown in FIGS. 3–3A, 4–4A, 5A–5D to provide a kit of stem and neck combinations to accommodate a variety of patients. It will be appreciated that by varying features such as the size of slots, the size of the tabs, offsetting tabs and slots, and the length of the tab and/or depth of the slot, a wide variety of stem and neck combinations could be provided in a kit of modular prostheses.

Figure 7A:
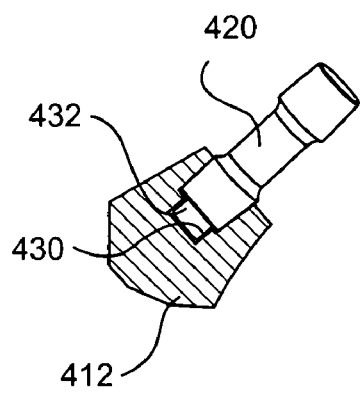
FIGS. 7A–D shows an example of a kit comprising a stem and a plurality of necks according to one embodiment.
Figure 7B:
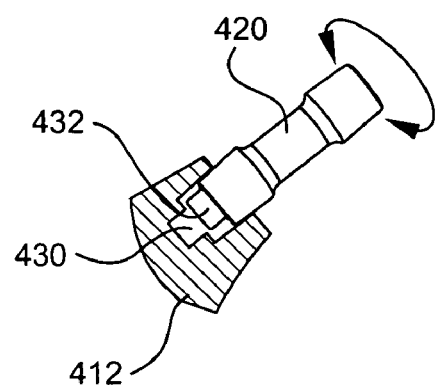
Figure 7C:
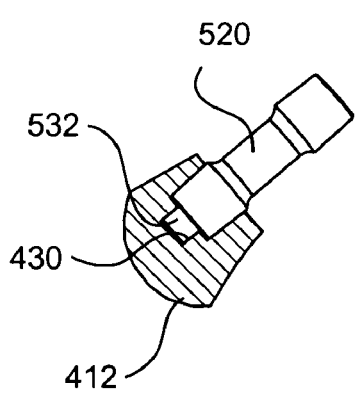
Figure 7D:
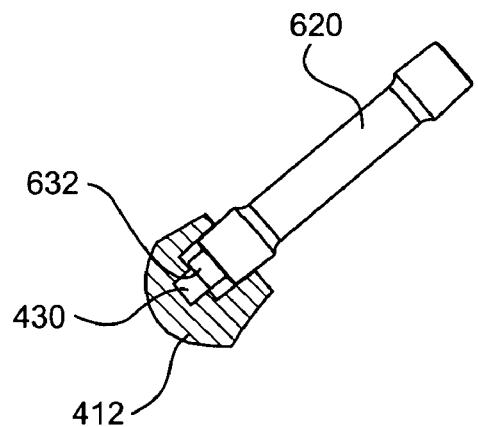

Examples of desirable and undesirable combinations of necks and stems are shown in FIGS. 7A–D and FIGS. 8A–F. In FIGS. 7A and 7B, a small stem 412 and a small high angle neck 420 are shown. The tab 432 on the end of the neck 420 and the slot 430 of the stem 412 are configured so that a small high angle neck 420 can taper lock with the stem 412 in only one position. In FIG. 7C, the same stem 412 as shown in FIGS. 7A–7B together with a small straight neck 520. The tab 532 of the small straight neck 520 and the slot 430 of the stem 412 are configured so that the tab 532 and the slot 430 can register, allowing the small straight neck 520 to taper lock with the stem 412 in any position. In FIG. 7D, the stem 412 is shown together with a large straight neck 620. The tab 632 on the large straight neck 620 and the slot 430 cannot register, preventing the large straight neck from taper locking with the stem 412 in any position.

Figure 8A:
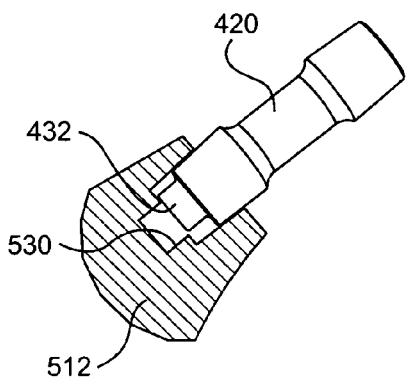
FIGS. 8A–F shows an example of a kit comprising a plurality of stems and necks according to an alternate embodiment.
Figure 8B:
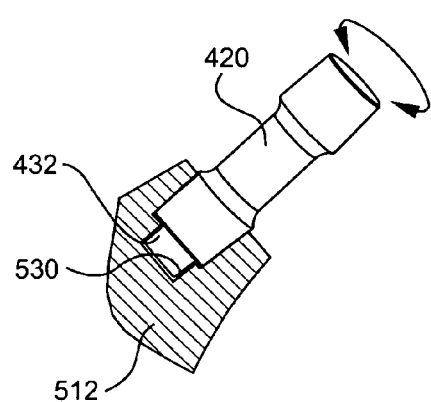
Figure 8C:
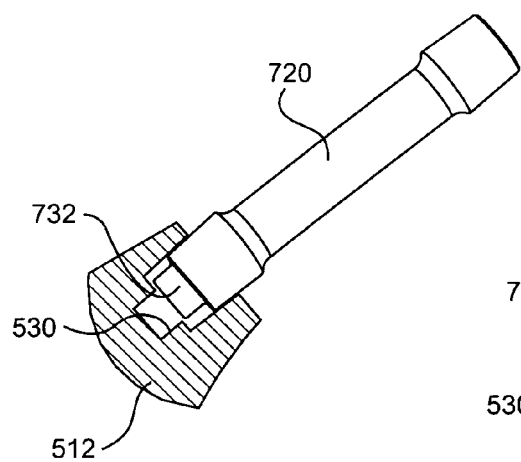
Figure 8D:
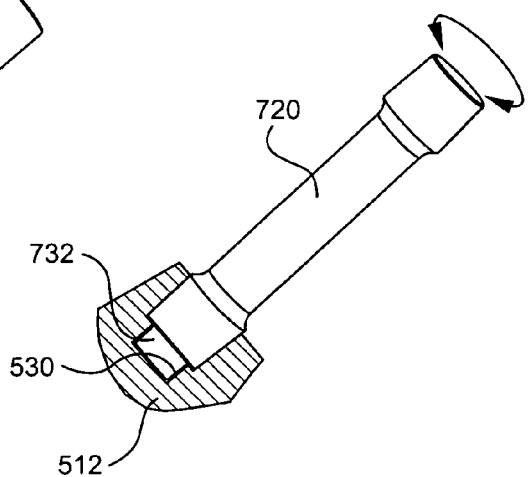
Figure 8E:
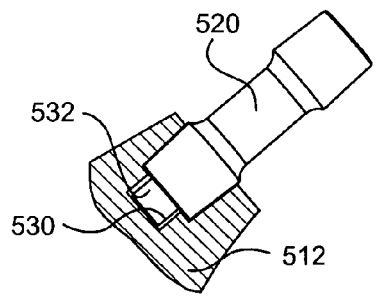
Figure 8F:
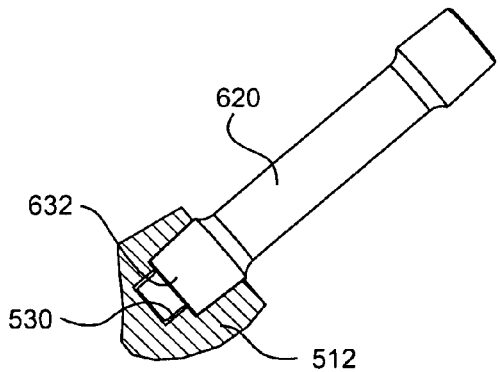

In FIGS. 8A–F, various neck and stem combinations are shown. A large stem 512 with a slot 530 is shown in FIGS. 8A–8B as being able to taper lock with the small high angle neck 420 in only one angular or circumferential position. In FIG. 8A, the neck 420 is shown as not being able to taper lock with the stem in a first circumferential position with respect to the longitudinal axis of the neck 420. In FIG. 8B, in which the neck 420 is rotated 180 degrees about its longitudinal axis with respect to its angular position in FIG. 4A, the neck 420 is shown as being able to taper lock in the stem 512. In FIGS. 8C–8D, the large stem 512 is shown as being able to taper lock with the large high angle neck 720 in only one position. The tab 732 and slot 530 prevents taper locking of the large high angle neck 720 in one position. More specifically, in FIG. 8C, the large neck 512 is shown as not being able to taper lock with the neck 720 in a first angular position. However, in FIG. 8D, when the neck 720 has been rotated about its longitudinal axis 180 degrees with respect to the position shown in FIG. 8C, the neck 720 can taper lock with the stem 512. In FIG. 8E, the small straight neck 520 is shown as being able to taper lock with the large stem 512 in at least one position. In FIG. 8F, the large straight neck 620 is shown as being able to taper lock with the large stem 512 in at least one position. It will be appreciated, that the above combinations are a small sampling of the possible combinations of necks and stems that are possible.

One or more embodiments of the present invention thus provides a modular prosthesis 10 kit comprising at least two differently sized stems, each stem including a tapered bore having a distal portion and a proximal portion and a neck registration element on the distal portion of the bore and a plurality of necks. Each has a tapered distal end and a stem registration element on the distal end of the neck. The plurality of necks includes a first neck having a stem registration element that can register with the neck registration element of at least one stem in more than one position, a second neck having a stem registration element that can register with the neck registration element of at least one stem in only one position, and a third neck having a stem registration element that cannot register with at least one neck in any position.

One or more embodiments of the present invention reduces the number of parts required to perform a hip or shoulder prosthesis. A greater number of offset and version options are provided by the modular prosthesis system of the present invention compared with prior systems. In addition, it is possible to provide customized neck versions and offsets. The modular prosthesis system of the present invention allows the practitioner to achieve a neck angle that substantially matches each patient's unique anatomy to allow a greater range of motion than in prior systems. This ensures minimal joint reaction force and correct stress transfer from the upper body to the femur through the ankle in hip systems. One or more embodiments of the present invention achieves optimal orientation of the femoral head, resulting in less stress on the acetabulum, reduced wear, and a reduced chance of dislocation.

Figure 9:
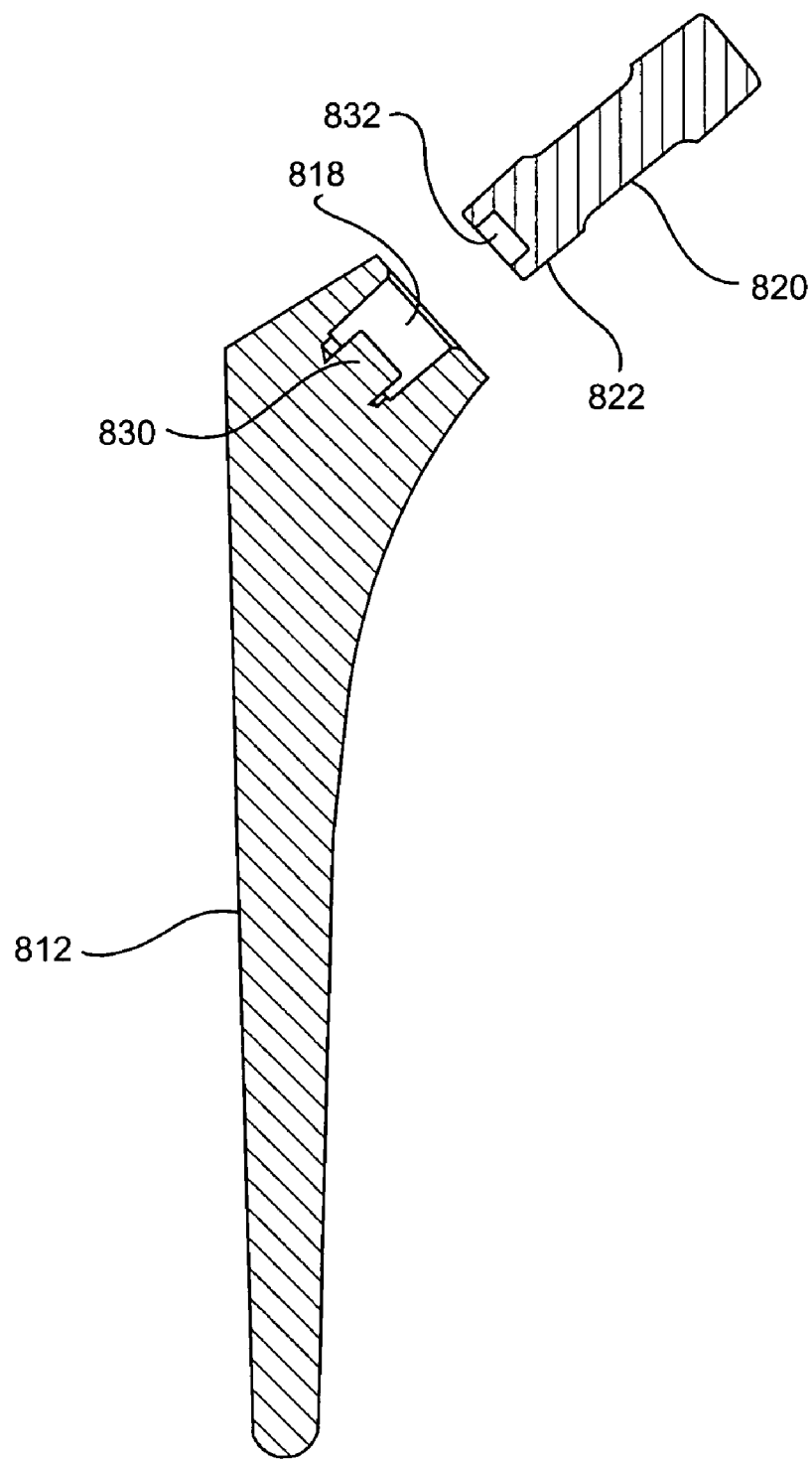
FIG. 9 is a cross-sectional view of a stem and a neck according to an alternate embodiment.

Although the invention herein has been described with reference to particular embodiments, it is to be understood that these embodiments are merely illustrative of the principles and applications of the present invention. For example, while the embodiments shown in FIGS. 1–8 show stem with neck registration elements including slots and necks with stem registration elements including tabs, this orientation could be reversed as shown in FIG. 9. In FIG. 9, the stem 812 is shown as having a tapered bore 818 and a neck registration element 830 including a shaped tab extending from the bore. The neck 820 is shown as having a tapered distal end portion 822 having a bore 832 formed on the distal end 822 adapted to cooperate with the neck registration element in the form of a tab 830 to either permit or prevent registration and taper locking of the stem 812 and the neck 820.

Figure 10:
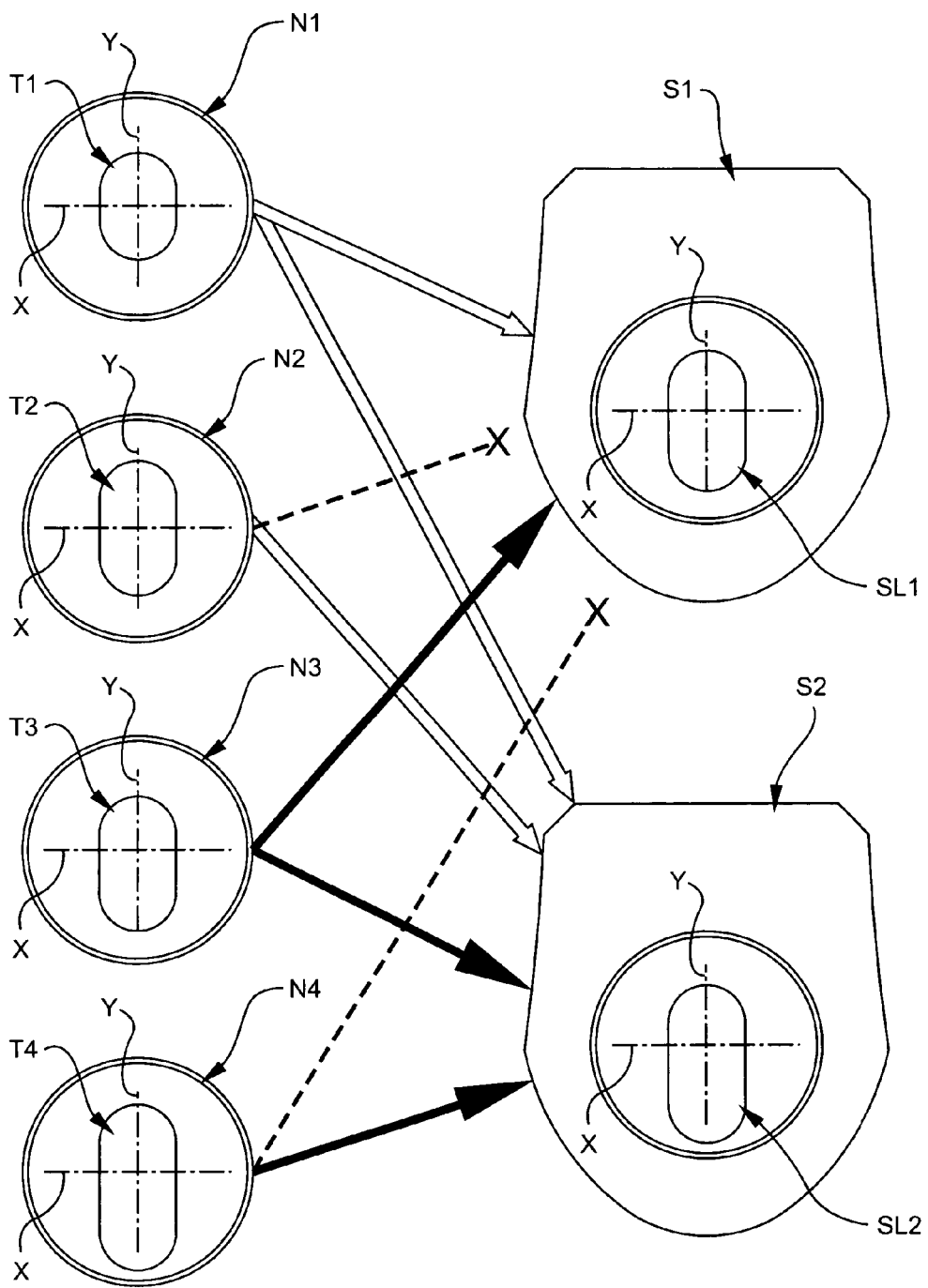
FIG. 10 is a schematic view showing possible combinations and fitting of a plurality of necks with a pair of stems according to one embodiment of the invention.

In one or more preferred embodiments of the invention, a kit or a system may include necks with four different types of stem registration element configurations and stems with two different types of neck registration element configurations, as shown in FIG. 10. In FIG. 10, the stem registration elements are shown as tabs and the neck registration elements are shown as slots. It will be understood, that this arrangement could be reversed so that the slots are on the ends of the necks and the tabs are associated with the stems. FIG. 10 is a schematic representation of such a system. It will be understood, of course, that the present invention should not be limited to any particular number of necks, stems, or configurations of neck registration elements and stem registration elements.

In FIG. 10, a first neck N1 has a tab T1, which is a relatively small tab. The tab T1 is coaxial with and substantially centrally located on the end of the neck N1, as indicated by the X and Y axes shown in FIG. 10. A second neck N2 has a tab T2, which is larger than the tab T1. The tab T2 is coaxial with and substantially centrally located on the end of the neck N2, as indicated by the X and Y axes shown in FIG. 10. A third neck N3 has a tab T3. The tab T3 is eccentric with respect to the end of the neck N3, as noted by the X and Y axes. Tab T3 is larger than tab T1, and according to one or more embodiments a portion of tab T3 is elongated in at least one direction along the Y axis. In the embodiment shown, the tabs T1, T2, and T3 are all substantially elliptical in cross section. Tab T3 is elongated along the major axis (the Y axis) of the ellipse. Neck N4 includes tab T4 eccentric with the end of the neck N4. Tab T4 is larger than tabs T1, T2, and T3. As shown in FIG. 10, tab T4 is elongated along its major axis (shown as the Y axis) in one direction.

The kit shown in FIG. 10 further includes two stems having different neck registration element configurations. Stem S1 includes a slot SL1 that is eccentric to the center of a bore formed in the stem S1. Slot SL1 is substantially the same size as the tab T3. Stem S2 includes a slot SL2 that is eccentric to the center of a bore form in the stem S2. Slot SL2 is substantially the same size as the tab T4. Slot SL2 is larger in at least one dimension compared to slot SL1. In the embodiment shown, slot SL2 in longer in one direction along the major or Y axis of the slot compared to SL1.

The solid lines terminating in arrows in FIG. 10 indicate that a particular neck can taper lock with certain stems in only one angular position with respect to the longitudinal axis of the neck. The dashed lines terminating with an "X" indicate that a particular neck cannot taper lock with certain stems in any angular position. The double line terminating with an arrow indicates that particular necks can taper lock with certain necks in two angular positions with respect to the longitudinal axis of the neck. Preferably, the two angular positions are 0 degrees and 180 degrees with respect to the longitudinal axis of the neck. Thus, according to the kit or system shown in FIG. 10, the following neck and stem taper lock combinations are possible as shown in Table I:

TABLE I

| Angular Position: | Stem Configuration = S1 | | Stem Configuration = S2 | |
| --- | --- | --- | --- | --- |
|  | 0° | 180° | 0° | 180° |
| Neck N1 | Yes | Yes | Yes | Yes |
| Neck N2 | No | No | Yes | Yes |
| Neck N3 | Yes | No | Yes | No |
| Neck N4 | No | No | Yes | No |

In addition, while the drawings show the stem registration elements and neck registration elements as being elliptical in cross section, other configurations or cross-sectional shapes are within the scope of the invention. Non-limiting examples of such shapes are shown in FIG. 11 and include square, triangular, rectangular, polygonal, hexagonal, octagonal, circular, diamond-shaped, or shaped like a bow-tie. Furthermore, while the Figures show modular prostheses the invention is not limited to prostheses. It will be understood that the term "stem" as used herein may be part of a prosthetic implant, or it may form part of an instrument, for example, including but not limited to a rasp, a broach, or a trial stem. It is therefore to be understood that numerous modifications may be made to the illustrative embodiments and that other arrangements may be devised without departing from the spirit and scope of the present invention as defined by the appended claims and their equivalents.

What is claimed is:

1. A modular prosthesis kit comprising:
   at least two differently sized stems, each stem including a tapered bore having a distal portion and a proximal portion and a neck registration element located in the distal portion of the bore; and
   a plurality of necks, each of the necks having a proximal end and a distal end, the distal end including a tapered portion configured to taper lock in the tapered bore and a stem registration element, the plurality of necks including a first neck having a stem registration element that cooperates with the neck registration element of first stem to permit the first neck to taper lock in the bore of said stem in one position and to prevent the first neck from taper locking in the bore of second stem in at least one position, the first stem in which the first neck taper locks being different from the second stem in which the first neck is prevented from taper locking, said first stem being a different size then said second stem.

2. The kit of claim 1, wherein the plurality of necks further includes at least one non-fitting neck having a stem registration element that prevents the at least one non-fitting neck from taper locking in the bore of at least one of the stems in any position.

3. The kit of claim 2, wherein the stem registration element on each neck includes a shaped tab extending longitudinally from the distal end of the neck and the neck registration element on each stem includes a shaped slot, wherein the tab of at least one of the non-fitting necks and the slot of the at least one stem are configured such that the tab of at least one of the non-fitting necks cannot register in the slot of the at least one stem to prevent the tapered end of the non-fitting neck to taper lock.

4. The kit of claim 3, wherein the tab on the non-fitting neck is larger than the slot of the at least one stem in at least one dimension.

5. The kit of claim 4, wherein the tab has a length dimension along the longitudinal axis of the stem and the slot has a depth dimension, and the length of the tab of the at least one non-fitting neck is greater than the depth of the slot of at least one stem.

6. The kit of claim 3, wherein the slots have a major axis and a minor axis and the tabs have a major axis and a minor axis.

7. The kit of claim 6, wherein the major axis of the tab of the at least one non-fitting neck is larger than the major axis of the slot of at least one stem.

8. The kit of claim 6, wherein the minor axis of the tab of at least one non-fitting neck is larger than the minor axis of the slot of at least one stem.

9. The kit of claim 6, wherein the tabs and slots are elliptical in cross-section.

10. The kit of claim 3, wherein the tab on the at least one non-fitting neck has a different shape than the slot of at least one of the stems.

11. The kit of claim 1, wherein the plurality of necks includes at least one fitting neck having a stem registration element that permits the at least one fitting neck to taper lock in the bore of the at least one of the stems in at least two positions.

12. The kit of claim 11, wherein the plurality of necks includes at least one non-fitting neck having a stem registration element that prevents the at least one non-fitting neck from taper locking in the bore of at least one pre-selected stem.

13. The kit of claim 11, wherein the stem registration element of each neck includes a shaped tab extending longitudinally from the distal end of the neck and the neck registration element of each stem includes a shaped slot, wherein the tab of the at the least one fitting neck and the slot of the at least one stem are configured such that the tab of the at least one fitting neck can register in the slot of the at least one stem in two positions to permit the tapered end of the at least one fitting neck to taper lock in the bore of the at least one stem.

14. The kit of claim 13, wherein the tab of the at least one fitting neck and the slot of stem each have a major axis and a minor axis.

15. The kit of claim 14, wherein the size of the tab of the at least one fitting neck and the slot of at least one of the stems are substantially the same.

16. The kit of claim 14, wherein the tab of the at least one fitting neck is smaller in at least one dimension than the slot of the at least one stem.

17. The kit of claim 1, wherein the stem registration element includes a shaped tab extending longitudinally from the distal end of the neck and the neck registration element includes a shaped slot in the distal portion of the bore such that the tab of the first neck can register with the slot of first one of the stems to allow the tapered end portion of the first neck to taper lock in the bore of said stem in at least one position and the tab of the first neck cannot register in the slot of second stem to prevent the tapered end portion of the first neck from taper locking in the bore of said second stem in one position.

18. The kit of claim 17, wherein the tab of at least one of the first necks is eccentric with respect to the center of the tapered end of the neck such that the tab cannot register with the slot in the bore of second stem and prevents taper locking of the tapered end of the first neck in the bore of said second stem in at least one position.

19. The kit of claim 18, wherein the slot in the bore of the at least one stem and the tab of the first neck are configured to register such that the tapered end of the first neck can taper lock in the bore of the at least one stem in at least one position.

20. The kit of claim 19, wherein the slot of at least one of the stems is eccentric with respect to the center of the bore.

21. The kit of claim 17, wherein each of the shaped slots has a major axis and a minor axis and the each of the tabs have a major axis and a minor axis.

22. The kit of claim 21, wherein the tabs and slots are elliptical in cross-section.

23. The kit of claim 21, wherein the tab and the slot are substantially the same size in cross-section.

24. The kit of claim 1, wherein the stem registration element of each neck includes a slot and the neck registration element of each stem includes a tab.

25. A modular prosthesis kit comprising:
   a plurality of differently sized stems, each stem including a tapered bore having a distal portion and a proximal portion and a neck registration element on the distal portion of the bore;
   a plurality of necks having different lengths and angles, each of the necks having a conical taper on a distal end of the neck configured to taper lock in a bore and a stem registration element longitudinally extending from the distal end of each neck, wherein a first neck of a predetermined length and angle has stem registration element that can register with the neck registration element of at least one of the stems in only one position to permit the first neck to taper lock with bore of the at least one stem in only one position and a second neck of a predetermined length and angle has a stem registration element that can register with at least one of the stems in multiple positions and permit the second neck to taper lock in the bore of the at least one stem in multiple positions, and wherein the stem registration element of one of the plurality of necks prevents that neck from taper locking in the bore of one of the plurality of stems.

26. The kit of claim 25, further comprising a third neck of a predetermined length and angle having a stem registration element that cannot register with the neck registration element of at least one stem in any position preventing taper locking of the third neck with the at least one stem in any position.

27. The kit of claim 26, wherein the stem registration element includes a shaped tab, and the neck registration element includes a shaped slot.

28. The kit of claim 27, wherein the tab of the first neck is eccentric with respect to the tapered end of the neck.

29. The kit of claim 27, wherein the tab of the second neck is smaller than the slot in at least one dimension.

30. The kit of claim 29, wherein the tab and slot have a cross-sectional shape with a major axis and a minor axis.

31. The kit of claim 30, wherein the tab and slot have an elliptical cross-sectional shape.

32. The kit of claim 30, wherein the major axis of the tab is shorter than the major axis of the slot.

33. The kit of claim 27, wherein the cross-sectional shape and size of the tab and the slot are substantially similar.

34. The kit of claim 27, wherein the tab of the third neck is larger in one dimension than the shaped slot of at least one stem in a corresponding direction.

35. The kit of claim 34, wherein the tab of the third neck has a length dimension along the longitudinal axis of the neck that is greater than the depth of the shaped slot of at least one stem.

36. The kit of claim 34, wherein the shaped tab of the third stem and the shaped slot of at least one neck each have a major axis and a minor axis.

37. The kit of claim 26, wherein the stem registration element of each neck includes a shaped slot and the neck registration element of the stems includes a shaped tab.

38. A modular prosthesis kit comprising:
at least two differently sized stems, each stem including tapered bore having a distal portion and a proximal portion and a neck registration element on the distal portion of the bore;
a plurality of necks, each neck having a tapered distal end and a stem registration element on the distal end of the neck, wherein the plurality of necks includes a first neck having a stem registration element that can register with the neck registration element of at least one stem in more than one position, a second neck having a stem registration element that can register with the neck registration element of at least one stem in only one position, and a third neck having a stem registration element that cannot register with at least one neck registration element of at least one stem in any position.

39. A modular prosthesis kit comprising:
a plurality of stems, each stem including a conically tapered bore having an open end and a bore portion opposite said open end, said bore including a registration element therein;
a plurality of necks each having a conically tapered end for mating with the tapered bores of each of said stems and a registration element for engaging the bore registration element on at least one of said stems in a manner allowing a locking engagement of said tapered bore and said tapered neck portion in at least one circumferential position of said tapers;
at least one neck of said plurality of necks having a registration element allowing locking engagement with at least one stem in at least two circumferential positions of said tapers; and
at least one neck of said plurality of necks having a registration element which engages said registration element of at least one of said stems in a manner which prevents said tapered bore and said tapered neck portion from locking engagement in any circumferential position.

40. The kit of claim 39, wherein the registration element in the bore includes a slot.

41. The kit of claim 40, wherein the registration element on the necks includes a tab extending longitudinally from an end thereof.

42. The kit of claim 41, wherein the registration elements include a major axis and a minor axis.

43. The kit of claim 42, wherein the registration elements are substantially elliptical in shape.

44. The kit of claim 43, wherein the tab on the neck of said plurality of necks having a registration element allowing engagement with at least one stem in at least one circumferential position is elongated along the major axis in one direction.

45. The kit of claim 44, wherein the tab on the at least one neck of said plurality of necks having a registration element which prevents locking engagement of said neck in any circumferential position is elongated along the major axis in one direction.

46. A modular prosthesis kit comprising:
a plurality of stems having a conically tapered locking portion extending along an axis, said stem conically tapered locking portions including a registration element;
a plurality of necks having a conically tapered locking portion for lockingly engaging said stem tapered locking portion along said axis, said neck conically tapered locking portion including a registration element selectively engagable with said stem registration element to allow or prevent a locking engagement of said stem and neck tapered locking portions;
each of said plurality of necks having a registration element engagable with the stem registration element of at least one of said plurality of stems in at least one circumferential position about said axis allowing the locking engagement of said conically tapered stem and neck locking portions and at least one neck of said plurality of necks having a registration element which engages the registration element of at least one of said stems in a manner which prevents the engagement of said stem and neck locking portions in any circumferential position.

47. The kit as set forth in claim 46 further comprising at least one neck of said plurality of necks having a registration element allowing locking engagement with at least one stem in at least two circumferential positions about said axis.

* * * * *

UNITED STATES PATENT AND TRADEMARK OFFICE
CERTIFICATE OF CORRECTION

PATENT NO. : 7,135,044 B2  Page 1 of 1
APPLICATION NO. : 10/796168
DATED : November 14, 2006
INVENTOR(S) : Renen Bassik, John David Czajkowski and Thomas Francis McCarthy It is certified that error appears in the above-identified patent and that said Letters Patent is hereby corrected as shown below:

Title Page, Item (75) Inventors: "Mc Carthy" should read --McCarthy--.
Column 1, line 9, the word "prevents" should read --prevent--.
Column 3, line 13, the word "stem" should read --stems--.
Column 3, line 17, the word "has" should read --have--.
Column 3, line 21, the word "that" should read --than--.
Column 3, line 48, insert a comma --,-- after the word "position".
Column 4, line 31, the word "an" should read --a--.
Column 5, line 24, delete the word "includes".
Column 5, line 40, the word "prevents" should read --prevent--.
Column 6, line 22, insert a comma --,-- after the number "3".
Column 6, line 57, delete the word "by".
Column 8, line 61, the word "prevents" should read --prevent--.
Column 9, line 13, insert a comma --,-- after the word "bore".
Column 9, line 46, the word "stem" should read --stems--.
Column 10, line 28, the word "form" should read --formed--.
Column 12, line 37, insert the word --the-- after the word "of".
Column 12, line 49, the word "have" should read --has--.
Column 13, line 46, the words "tapered bore" should read --a tapered bore--.

Signed and Sealed this

Eighteenth Day of September, 2007

JON W. DUDAS
*Director of the United States Patent and Trademark Office*